US010433882B2

(12) United States Patent
O'Neil et al.

(10) Patent No.: US 10,433,882 B2
(45) Date of Patent: Oct. 8, 2019

(54) IMPLANT DRIVER

(71) Applicant: DePuy Synthes Products, Inc., Raynham, MA (US)

(72) Inventors: Michael O'Neil, Raynham, MA (US); Zoher Bootwala, Raynham, MA (US); Joseph Peterson, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 431 days.

(21) Appl. No.: 15/199,263

(22) Filed: Jun. 30, 2016

(65) Prior Publication Data

US 2018/0000526 A1     Jan. 4, 2018

(51) Int. Cl.
| A61B 17/70 | (2006.01) |
|---|---|
| A61B 17/86 | (2006.01) |
| B25B 23/06 | (2006.01) |
| A61B 17/16 | (2006.01) |
| A61B 17/88 | (2006.01) |

(Continued)

(52) U.S. Cl.
CPC ...... *A61B 17/7082* (2013.01); *A61B 17/1604* (2013.01); *A61B 17/1615* (2013.01); *A61B 17/1624* (2013.01); *A61B 17/1671* (2013.01); *A61B 17/8875* (2013.01); *A61B 50/20* (2016.02); *A61B 50/30* (2016.02); *A61B 90/39* (2016.02); *A61B 17/865* (2013.01); *A61B 90/361* (2016.02); *A61B 2034/2055* (2016.02);

(Continued)

(58) Field of Classification Search
CPC .............. A61B 17/7082; A61B 17/865; A61B 17/8875
See application file for complete search history.

(56) References Cited

U.S. PATENT DOCUMENTS

| 6,096,042 A | 8/2000 | Herbert |
| 8,087,325 B2 * | 1/2012 | Neubardt ............... A61B 90/98 206/347 |

(Continued)

FOREIGN PATENT DOCUMENTS

| CA | 2324742 A1 * | 4/2002 | ............. B25B 23/00 |
| EP | 0 512 262 | 11/1992 | |

OTHER PUBLICATIONS

International Search Report and Written Opinion (PCT/US2017/039854); dated Oct. 26, 2017.

*Primary Examiner* — Nicholas W Woodall
(74) *Attorney, Agent, or Firm* — Dunlap Codding, P.C.

(57) ABSTRACT

An apparatus for inserting implants in a bone comprising a frame having a cartridge receiving chamber and a barrel. A cartridge defining a plurality of chambers is positioned in the cartridge receiving chamber so the chambers are selectively alignable with a longitudinal passage of the barrel. At least one instrument is positioned in one of the chambers, and a plurality of implants is positioned in the other chambers. A drive assembly is engageable with the instrument and the implants. The drive assembly is slidably and rotatably disposed in the frame and is moveable between a retracted position, an engaging position wherein the distal end of the drive assembly is positioned to engage the selected one of the instrument and the implants, and an extended position wherein the drive assembly extends through the chamber to transport the selected one of the instrument or the implant from the chamber to the distal end of the barrel.

16 Claims, 9 Drawing Sheets

(51) Int. Cl.
- *A61B 50/30* (2016.01)
- *A61B 90/00* (2016.01)
- *A61B 50/20* (2016.01)
- *A61B 50/00* (2016.01)
- *A61B 34/20* (2016.01)

(52) U.S. Cl.
CPC .......... *A61B 2050/0065* (2016.02); *A61B 2050/3008* (2016.02)

(56) References Cited

U.S. PATENT DOCUMENTS

| | | |
|---|---|---|
| 2002/0016595 A1 | 2/2002 | Michelson |
| 2006/0053986 A1* | 3/2006 | Ward .................. B25G 1/085 81/490 |
| 2006/0243616 A1 | 11/2006 | Caron |
| 2010/0241129 A1 | 9/2010 | Markey et al. |
| 2010/0331852 A1 | 12/2010 | Neubardt |

* cited by examiner

IMPLANT DRIVER

BACKGROUND

Techniques and systems are known for correcting and stabilizing bones, including the bones of the spine. Stabilization of the spine for various conditions, such as degenerative disk disease, scoliosis, spondylolisthesis, and spinal stenosis, by way of example, often require attaching implants to the spine and then securing the implants to spinal rods. Such spinal fixation devices can immobilize the vertebrae of the spine and can alter the alignment of the spine over a large number of vertebrae by connecting at least one elongate rod to the sequence of selected vertebrae. These rods can span multiple vertebrae. The spine anatomy, however, rarely allows for three or more implants to be directly in line. In order to allow for this irregularity, the rod must be contoured to the coronal and sagittal planes.

Spinal fixation has become a common approach in fusion of vertebrae and treating fractures and the above listed spinal disorders. A common device used for spinal fixation is a bone fixation plate assembly. Typical bone fixation plate assemblies have a relatively flat, rectangular plate with a plurality of apertures therethrough. Another option is an implant fixation system that locks a rod to several vertebrae. In these systems, as with other spinal fixation systems, various fasteners, such as bone screws and spacers, are used to secure the implant fixation assembly to the desired and targeted vertebrae of the patient. These screws vary in design and shape, depending upon their desired location and use.

Screws, such as polyaxial, monoaxial, and uniaxial screws, are frequently used as fasteners in implantation fixation systems. Once these screws are set in a desired position, the screws are securely fixed in that position to minimize or eliminate movement of the vertebra. This is typically accomplished with a fixation system that securely engages the screw.

When screws are applied to a bone, multiple steps may be performed to apply the screw. First, an initial pilot hole may be made in the bone by an awl for placement of the screw. Then, a drill bit may be used to extend the pilot hole, and in some cases the hole may be tapped. Then, the screw can be applied into the tapped hole. This sequence requires the use of three separate steps and instruments, plus a driver for placing the screw into the tapped hole. Switching from instrument to instrument takes time and there are often challenges in locating the hole placed within the soft and the boney tissue. Each added step increases the time, and thus risk of infection, as new instruments are passed into the surgical site. In addition, current instruments can have variable levels of surgical effectiveness due to loss of sharpness following use in multiple cases and/or re-processing (e.g., awl, drill or tap, or driver tip) or due to drift in torque limiting features following re-processing. Lastly, current non- or pre-sterile screws often require the operating room staff to handle and touch the devices increasing risk of infection and/or damage to the clinician's gloves.

DETAILED DESCRIPTION OF EXEMPLARY EMBODIMENTS

Figure 1:
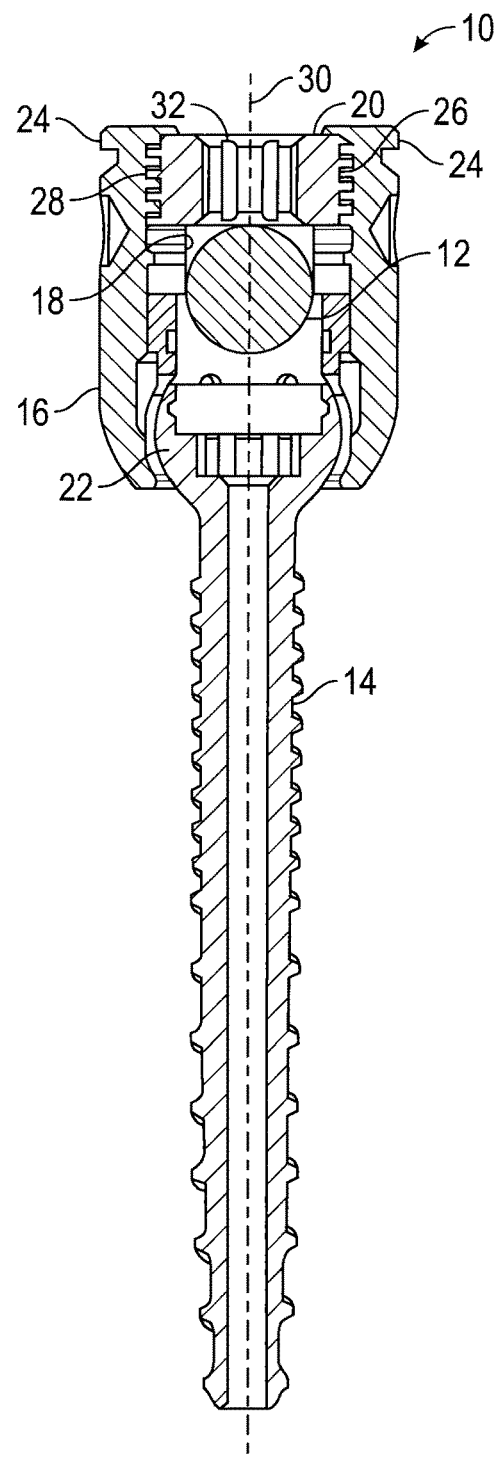
FIG. 1 is a sectional view of a prior art bone fixation element including an implant.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments, or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having," and any variations thereof, are intended to cover a non-exclusive inclusion. For example, a process, method, article, or apparatus that comprises a list of elements is not necessarily limited to only those elements, and may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B is true (or present).

In addition, use of the "a" or "an" are employed to describe elements and components of the embodiments disclosed herein. This is done merely for convenience and to give a general sense of the inventive concepts. This description should be read to include one or at least one and the singular also includes the plural unless it is obvious that it is meant otherwise.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to the drawings, FIG. 1 illustrates an exemplary embodiment of a bone fixation element 10 for use in a spinal fixation procedure to interconnect a rod 12 with a patient's vertebra. Broadly, the bone fixation element 10 includes a first implant 14 (that can also be referred to as a "screw" or a "bone anchor") for securing the bone fixation element 10 to a patient's vertebra, a rod receiving head 16 having a rod-receiving channel 18 for receiving the rod 12, and a second implant (that can also be referred to as a "locking cap") 20, for securing the rod 12 in the rod-receiving channel 18 in an implanted configuration. The first implant 14 is shown to include an enlarged head portion 22 which is received within an inner spherical cavity formed in rod receiving head 16 so that the first implant 14 can poly-axial rotate with respect to the rod receiving head 16. Alternatively, the first implant 14 may be formed integral with the rod receiving head 16 to form a monolithic structure which is referred to as a mono-axial pedicle screw or hook.

The rod receiving head 16 has a pair of arms 24 which define the rod-receiving channel 18. The arms 24 include a plurality of threads 26 on an inner surface thereof for threadably receiving the second implant 20.

The second implant 20 is shown to be in the form of a one piece implant including a plurality of external threads 28 threadingly engageable to the plurality of threads 26 on the inner surface of the arms 24 and an internal bored 30 defined by a plurality of internal ridges 32

Exemplary embodiments of pedicle screws include those described in International Patent Application No. PCT/US2008/070670, filed on Jul. 21, 2008, entitled "Polyaxial Bone Fixation Element," International Patent Application No. PCT/US2006/015692, filed on Apr. 25, 2006, entitled "Bone Anchor with Locking Cap and Method of Spinal Fixation," and International Patent Application No. PCT/CH1997/00236, filed on Jun. 16, 1997, entitled "Device for Connecting a Longitudinal Support with a Pedicle Screw," the contents of which are hereby incorporated by reference in their entirety. It should be understood, however, that the inventive concepts disclosed herein are not limited in use to any particular type of implant or pedicle screw. By way of example, the inventive concepts disclosed herein may be used to dispense other types of implants, such as pedicle screws and set screws, by way of example.

Figure 2:
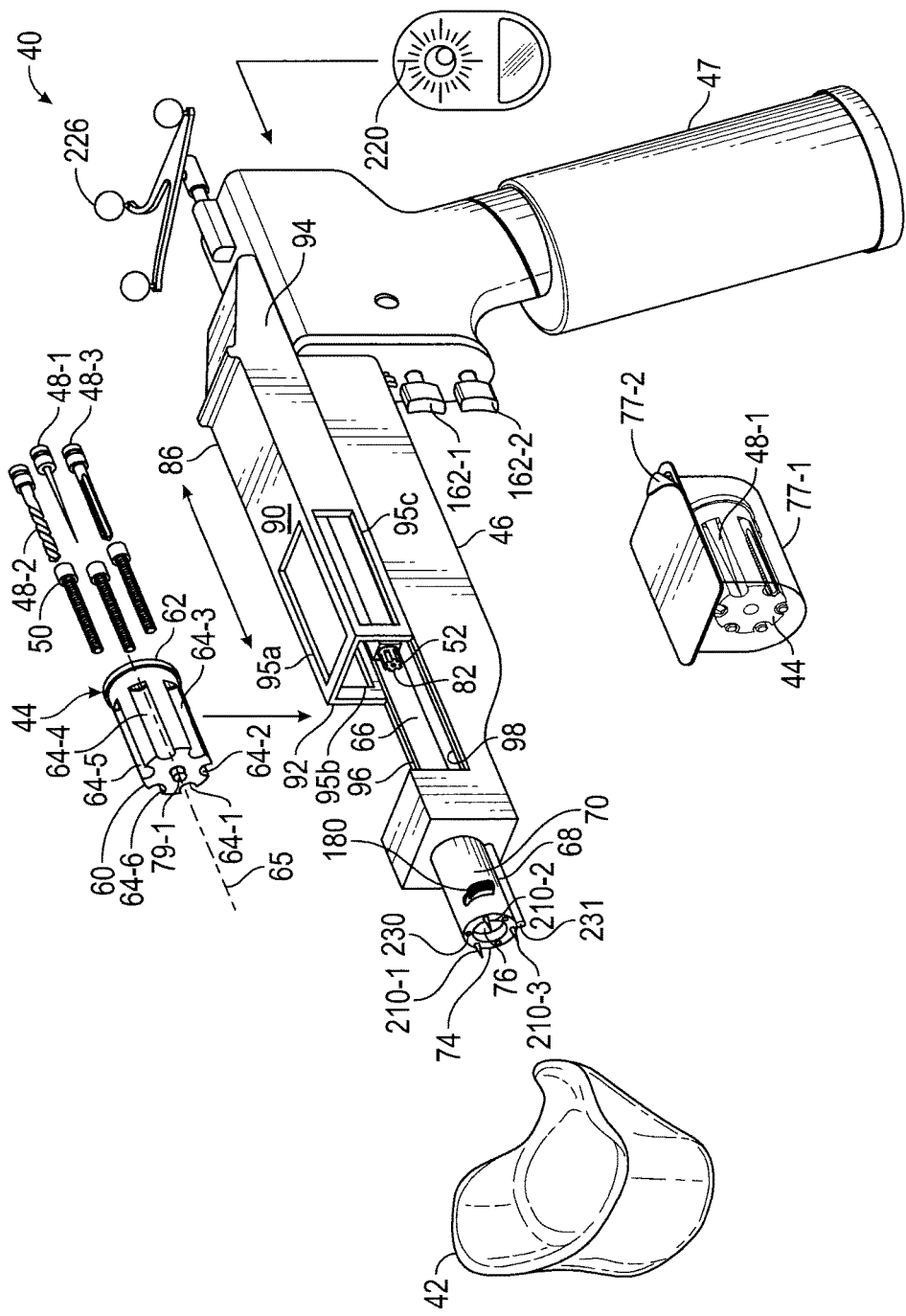
FIG. 2 is an exploded, perspective view of an apparatus constructed in accordance with the inventive concepts disclosed herein.

Referring now to an illustrative embodiment of FIG. 2, shown therein and designated by a reference numeral 40 is an apparatus for inserting multiple implants (such as the first implant 14), one at a time, into a bone 42. The apparatus 40 improves ease, accuracy, efficiency, and determination of the location of intraoperative placement of the first implant 14, for example, into the bone 42, thereby reducing risks associated with surgery, such as the potential infection.

In general, the apparatus 40 includes a frame 46 having a handle 47. The frame 46 supports a cartridge 44 which in one embodiment can house at least one instrument 48 and at least one implant 50. The frame 46 further supports a drive assembly 52. In the embodiment shown, the apparatus 40 uses the instrument 48 to perform work on the bone 42 (e.g., form a threaded hole in the bone 42). In this embodiment, the instrument 48 can be characterized as an awl 48-1, a drill bit 48-2, and a tap 48-3. As will be discussed below, the apparatus 40 is designed to engage and retract multiple instruments 48 in a sequential process (i.e., awl 48-1, drill bit 48-2, and tap 48-3) to form the threaded hole in the bone 42, and then to place the implant 50 into the threaded hole. The apparatus 40 is designed to perform the entire process while the apparatus 40 is continuously registered with the bone 42. To accomplish this, the apparatus 40 is designed to move the instruments 48, one at a time, from a retracted position to a driving position, and vice-versa while co-axially aligning the instruments 48 in at least the driving position. This avoids challenges in locating the hole as well as decreasing the risk of collateral tissue injury during location and placement of the various instruments 48 and the implant 50.

The cartridge 44 has a first end 60, a second end 62, and a plurality of chambers 64 extending through the cartridge 44 from the first end 60 to the second end 62. The chambers 64 are offset relative to each other along a circumferential direction and also extend in a substantially parallel relationship around a central axis 65 of the cartridge. In this example, the cartridge 44 is provided with six chambers 64 that are designated by way of example as 64-1, 64-2, 64-3, 64-4, 64-5 and 64-6. At least one instrument 48 is supported by the cartridge 44 with one instrument 48 being positioned within a particular one of the chambers 64. Further, at least one implant 50 is supported by the cartridge 44 with one implant 50 being positioned within a particular one of the chambers 64. In the example shown, the cartridge 44 supports three instruments 48 (e.g., the awl 48-1, the drill bit 48-2, and the tap 48-3, and three implants 50). The number of chambers 64 can vary depending upon the number of instruments 48 and the number of implants 50 to be supported by the cartridge 44. A plurality of retaining members 67 (FIGS. 4-7) extend into the chambers 64 for releasably supporting the instruments 48 and the implants 50 in the chambers 64. The retaining members 67 may be a detent or any other suitable device or structure.

The frame 46 at least partially surrounds and defines a cartridge receiving chamber 66 and is provided with a barrel 68 extending from the cartridge receiving chamber 66. The barrel 68 has a sidewall 70, a proximal end 72, a distal end 74, and a longitudinal passage 76 extending through the barrel 68 from the proximal end 72 to the distal end 74 and is configured to receive and position a selected instrument 48 or implant 50 for use at the distal end 74 of the barrel 68. The frame 46 is configured and sized to receive and support the cartridge 44 in the cartridge receiving chamber 66 such that the cartridge 44 is rotated in chamber 66.

In this embodiment, the cartridge 44 having the instruments 48 and the implants 50 loaded into the chamber 64 can be provided in a predetermined set in a sealed container 77-1 having a removable tab 77-2. By using the instruments 48 in the predetermined set to create the threaded hole for application of the implants 50 within the predetermined set, the instruments 48 have a consistent level of surgical effectiveness which reduces the problems discussed above due to loss of sharpness following use in multiple cases and/or re-processing (e.g., awl, drill or tap, or driver tip) or due to drift in torque limiting features following re-processing. Supporting the instruments 48 and the implants 50 in the cartridge 44 also reduces handling and touching of the instruments 48 and the implants 50 thereby reducing the risk of infection and/or damage to the clinician's gloves. Further, the cartridge 44, the implant(s) 50 and the instrument(s) 48 can be sterilized prior to or after the container 77-1 is sealed. For example, the cartridge 44, the implant(s) 50, and the instrument(s) 48 can be sterilized by treating with steam or a suitable biocide prior to insertion into the container 77-1. Alternatively, the cartridge 44, the implant(s) 50, the instrument(s) 48, and the container 77-1 can be sterilized by being subjected to an environment of at least 200 degrees Fahrenheit for a period of time suitable to kill or deactivate any microorganisms within the container 77-1.

The predetermined set of instruments 48 and implants 50 can be chosen so that the instruments 48 match the size and/or shape of the implants 50. For example, the size of the instruments 48 can be chosen so as to match the size of the implants 50 so that the threaded hole is formed to specifically receive the implants 50. Further, the instruments 48 and/or the implants 50 can be chosen and/or customized for a particular type of surgery, bone structure and/or placement of the implants 50, and/or a bone structure of a particular patient. Some surgeries may require different sizes and/or types of implants 50. In this situation, multiple cartridges 44 having different types of instruments 48 and/or implants 50 can also be provided as a set for a particular type of surgery so that the surgeon is provided with matched sets of instruments 48 and implants 50 to increase the effectiveness and efficiency of the surgery.

In the example shown, the frame 46 is provided with a pair of axially aligned grooves 78-1 and 78-2 (FIG. 3) extending forwardly and rearwardly with respect to the cartridge receiving chamber 66. The cartridge 44 is provided with a pair of axially aligned pins 79-1 and 79-2 with the pin 79-1 extending from the first end 60, and the pin 79-2 extending from the second end 62. When the cartridge 44 is inserted into the frame 46, the pins 79-1 and 79-2 are positioned within the grooves 78-1 and 78-2 so that the cartridge 44 can be rotated within the frame 46 to place one chamber 64 in a use position, and the remaining chambers 64 in a storage position.

Figure 3:
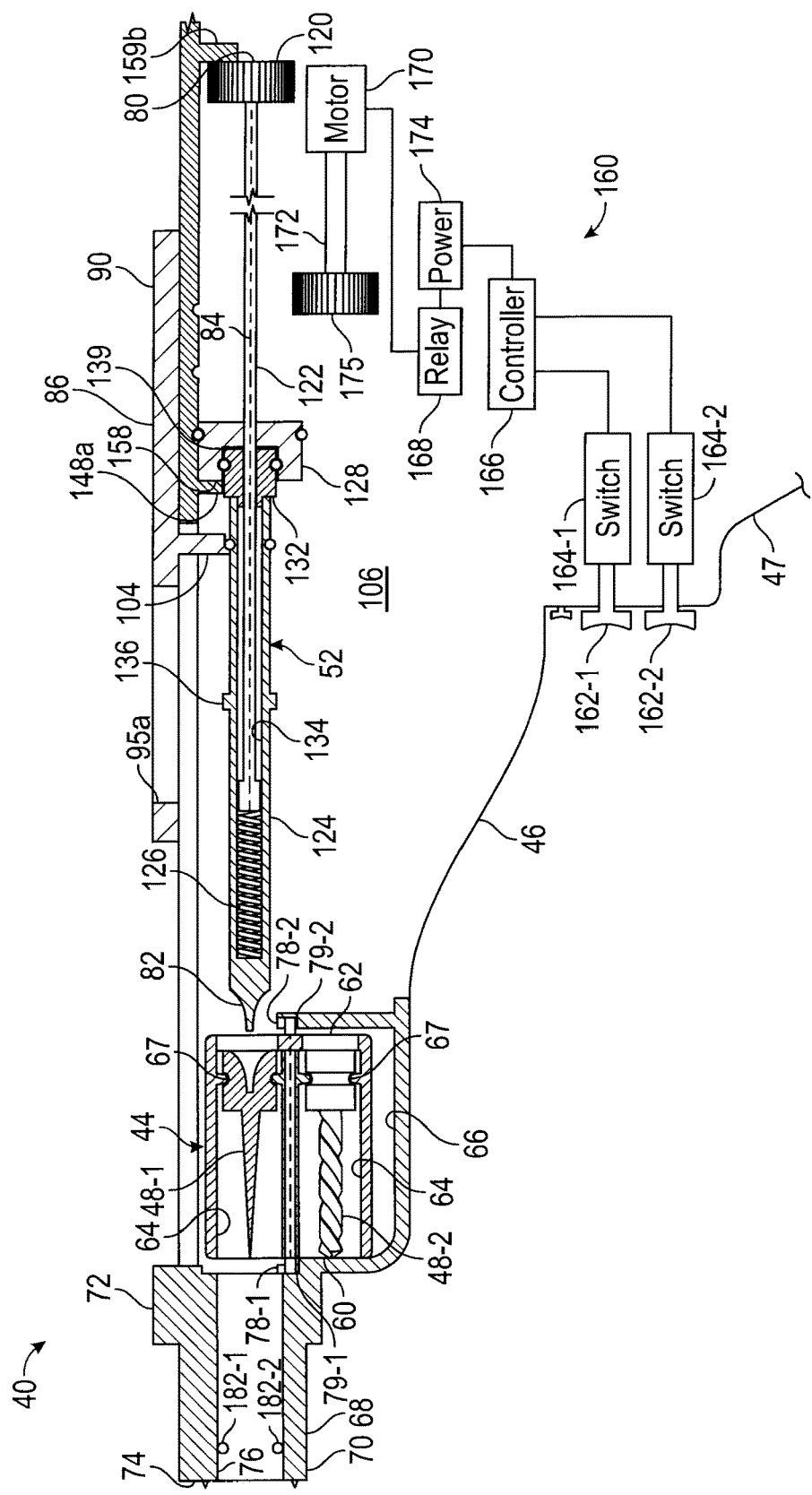
FIG. 3 is a cross-sectional and diagrammatic view of the apparatus illustrating a drive assembly in a retracted position.
Figure 4:
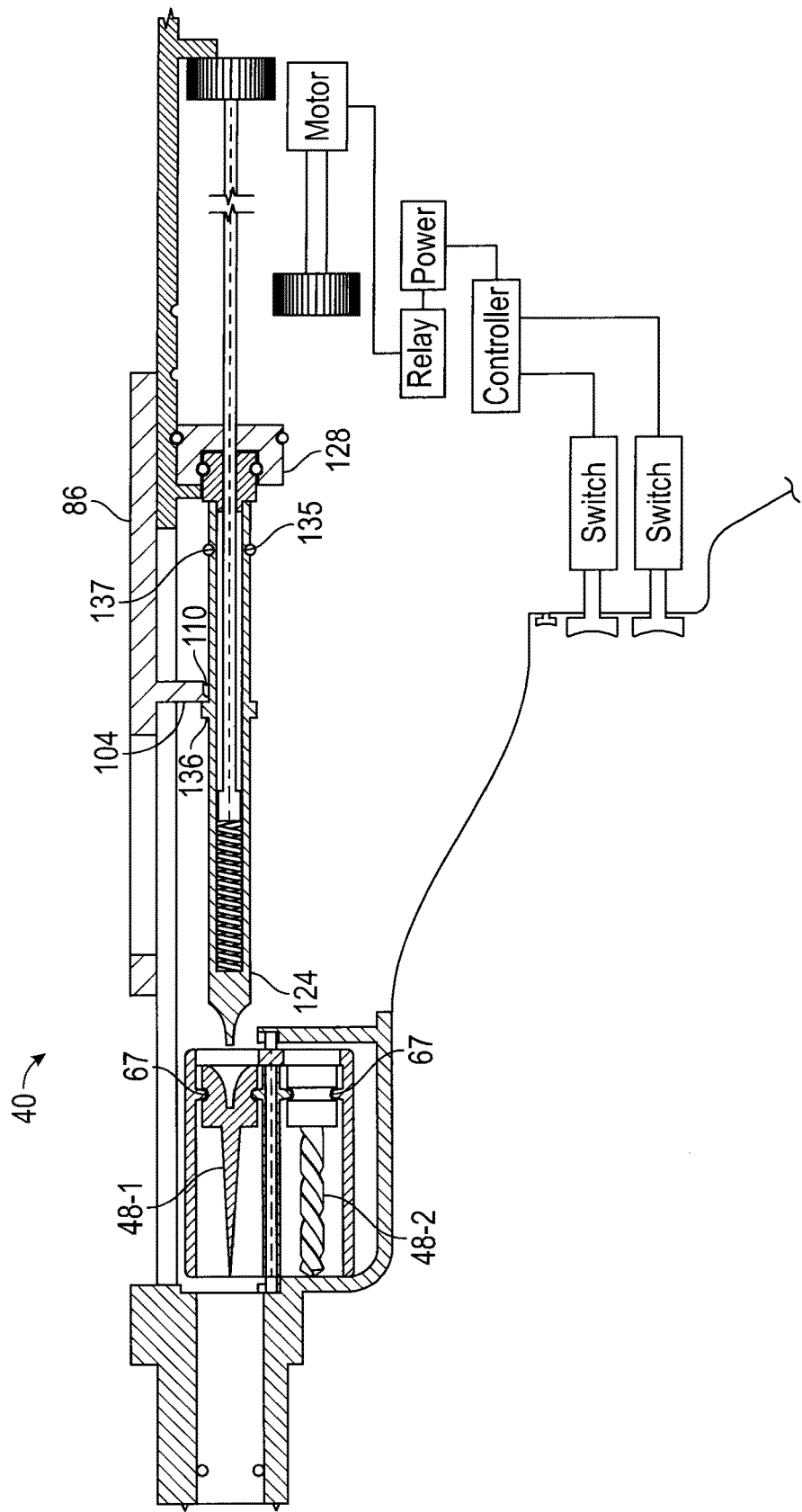
FIG. 4 is a cross-sectional and diagrammatic view of the apparatus illustrating the drive assembly in a partially extended position.
Figure 5:
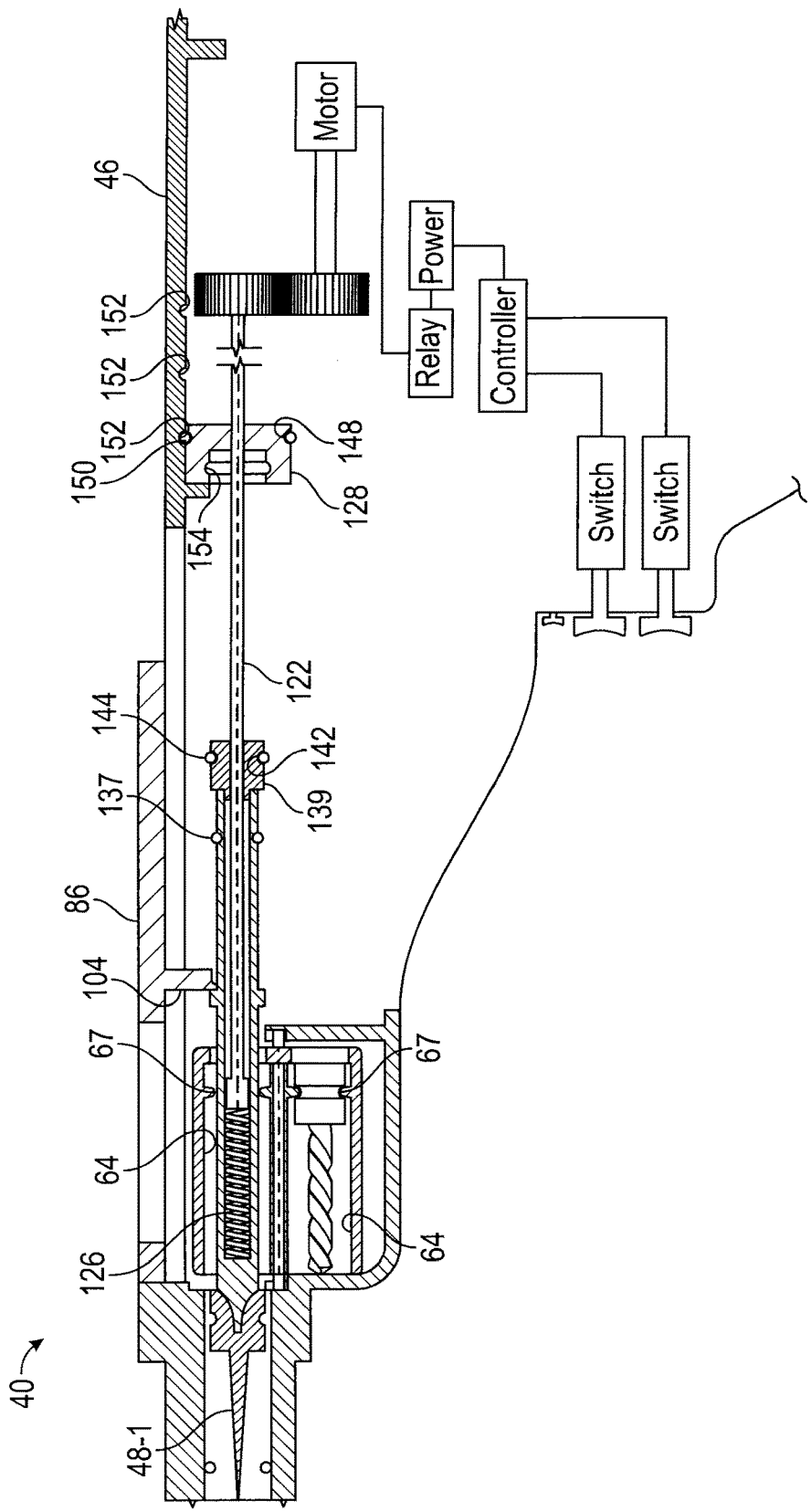
FIG. 5 is a cross-sectional and diagrammatic view of the apparatus illustrating the drive assembly in an extended position.
Figure 6:
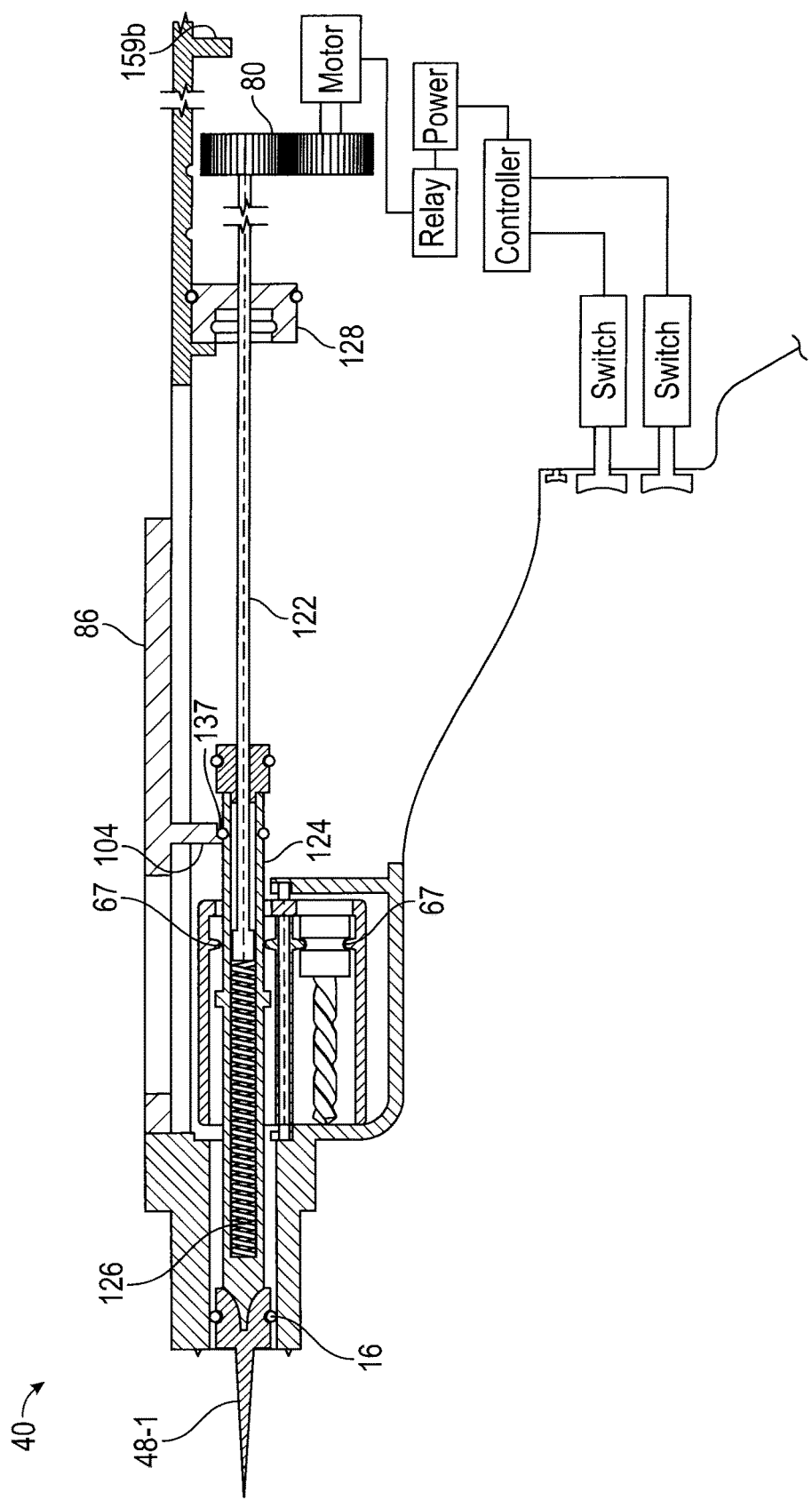
FIG. 6 is a cross-sectional and diagrammatic view of the apparatus illustrating the drive assembly in an released and extended position.
Figure 7:
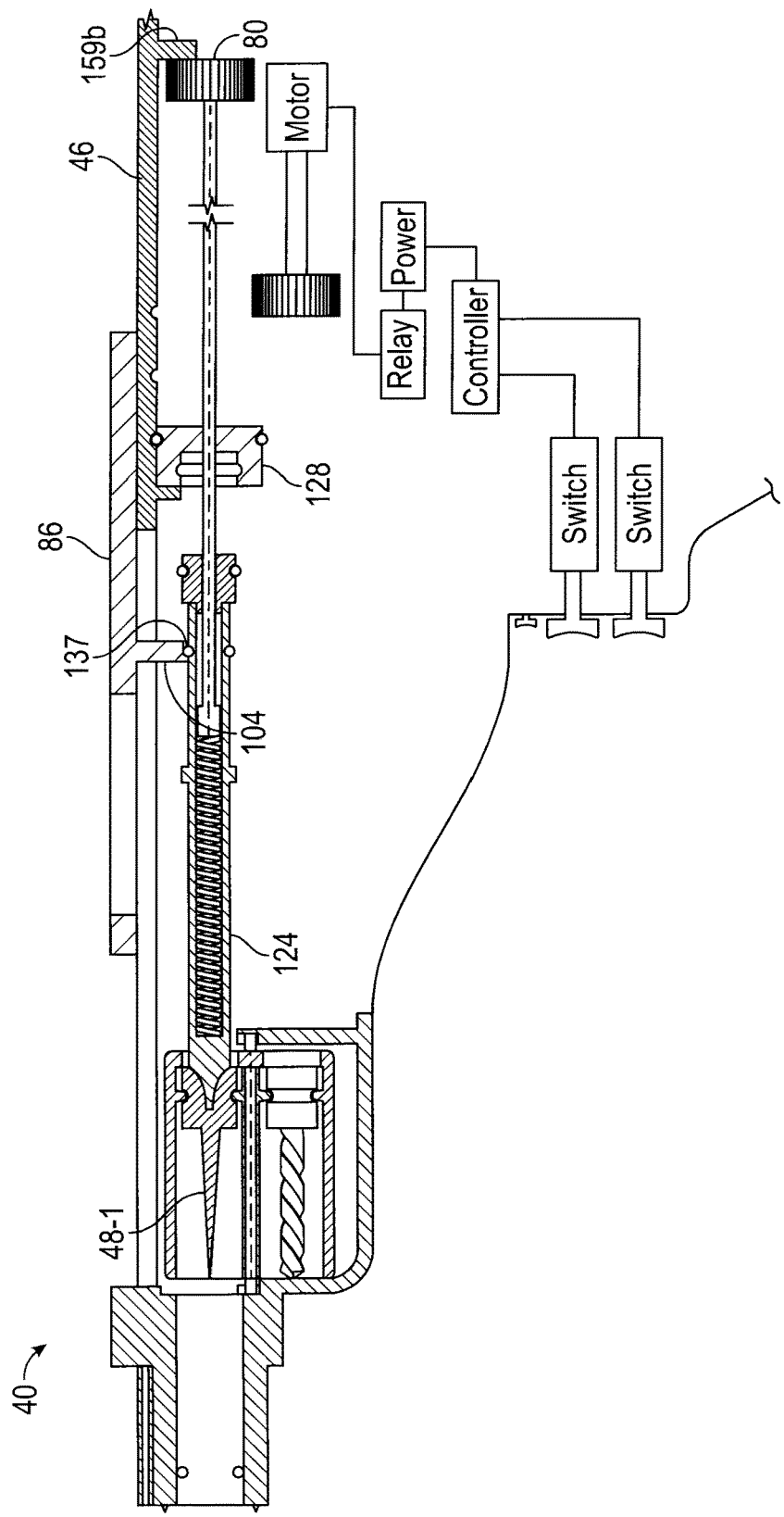
FIG. 7 is a cross-sectional and diagrammatic view of the apparatus illustrating the drive assembly in a partially retracted position.

With reference to FIGS. 2-7, the drive assembly 52 has a proximal end 80, a distal end 82, and a longitudinal axis 84. The chamber 64 in the use position is aligned with the longitudinal axis 84 of the drive assembly 52 and the longitudinal passage 76 of the barrel 68. The storage position is substantially parallel with, but offset from the longitudinal axis 84 of the drive assembly 52 and the longitudinal passage 76 of the barrel 68. The distal end 82 of the drive assembly 52 is engagable with the instrument 48 or the implant 50 that is in the use position. The drive assembly 52 is moveably and rotatably disposed in the frame 46 in a way that the drive assembly 52 is moveable between a retracted position (as shown in FIGS. 2 and 3), an engaging position (as shown in FIG. 4) wherein the distal end 82 of the drive assembly 52 engages either the instrument 48 or the implant 50, and a driving position (as shown in FIG. 6) wherein the distal end 82 of the drive assembly 52 extends distally beyond the engaging position.

As will be explained in more detail below, the distal end 82 of the drive assembly 52 is designed to be laterally and longitudinally connected to the instrument 48 to permit the drive assembly 52 to rotate and retract the instrument 48 back in the chamber 64 and to be laterally (and not longitudinally) connected with the implant 50 to permit the drive assembly 52 to rotate the implant 50, but not retract the implant back into the chamber 64. This permits the instruments 48 to be reused in forming multiple threaded holes configured to receive the implant 50, which is implanted within the bone 42 and not reused by the apparatus 40. In other words, the distal end 82 of the drive assembly 52 is engageable with the instrument 48 in a way that the instrument 48 can be rotated and retracted from the distal end 74 of the barrel 68 to the chamber 64 that is aligned with the longitudinal passage 76 of the barrel 68 upon moving the drive assembly 52 from the driving position to the retracted position. By way of contrast, the distal end 82 of the drive assembly 52 is engageable with the implant 50 in a way that permits rotation of the implant 50 but does not permit retraction of the implant 50 from the distal end 74 of the barrel 68 upon moving the drive assembly 52 from the driving position to the retracted position. This can be accomplished by designing a head of the implant 50 to have a loose fit (e.g., a square drive, phillips drive, or star drive) with the distal end 82 of the drive assembly 52, as will be explained in more detail below.

The apparatus 40 is also provided with a slide 86 engageable with the drive assembly 52. The slide 86 is a movable part of the apparatus 40 that moves the drive assembly 52 between the retracted position and the driving position and vice-versa. The slide 86 may be formed in a U-shape so as to have a top 90 connected to a first side 92 and a second side 94. The top 90, the first side 92, and the third side 94 may each include a window 95a-95c to allow the drive assembly 52 and the cartridge 44 to be observed when in use. The frame 46 is provided with a pair of tracks 96 and 98 that engage and support the first side 92 and the second side 94 to permit the first side 92 and the second side 94 to move in a linear fashion forwardly and rearwardly along the tracks 96 and 98. The slide 86 has a protrusion 104 (FIG. 3) extending downwardly from the top 90. The protrusion 104 extends downwardly from the top 90 into a driver cavity 106 surrounded by the top 90, the first side 92 and the second side 94. The protrusion 104 is provided with a notch 110 that is engageable with a portion of the drive assembly 52 in a manner to be described below.

Referring to FIGS. 3-7, the drive assembly 52 has the proximal end 80, the distal end 82, and the longitudinal axis 84. More particularly, the drive assembly 52 includes a power coupler 120, a driver shaft 122 connected to the power coupler 120, a driver 124 connected to the drive shaft 122 in a telescoping relationship such that the driver 124 is positionable between a retracted position and an extended position relative to the drive shaft 122, a biasing member 126 for biasing the driver 124 in the extended position relative to the drive shaft 122 (FIG. 6), and a collar 128 for holding the driver 124 in the retracted position (FIGS. 3 and 4).

The driver 124 has a first end 130 defining the distal end 82 of the drive assembly 52, a second end 132, and a bore 134 extending from the second end 132 towards the first end 130. The driver 124 also has an annular shoulder 136 extending outwardly and located for engagement with the protrusion 104 of the slide 86 and an annular groove 135 for receiving a retaining member 137 (FIG. 4), such as a round spring or detent, also located for engagement with the protrusion 104 to control longitudinal movement of the driver 124 in a manner to be discussed below.

The drive shaft 122 serves to transfer power from the power coupler 120 to the driver 124. The biasing member 126 (e.g., a coil spring) and a distal end of the drive shaft 122 are slidably positioned in the bore 134 of the driver 124 and secured therein with a cap 139 with the biasing member 126 positioned between the distal end of the drive shaft 122 and the first end 130 of the driver 124. The drive shaft 122 extends through the cap 139, and the drive shaft 122 and the cap 139 are keyed relative to one another (e.g., square shape, hex shape) so that the drive shaft 122 is longitudinally slidable relative to the cap 139, but rotation of the drive shaft 122 in either a clockwise or counterclockwise direction causes rotation of the driver 124. The cap 139 also has an annular groove 142 for receiving a retaining member 144 (FIG. 5), such as a round spring or detent, located for releasable engagement with the collar 128.

The collar 128 has a central opening 146 through which the drive shaft 122 extends and an annular groove 148 for receiving a retaining member 150, such as a round spring or detent, which is receivable in a groove 152 of the frame 46 for securing the collar 128 relative to the frame 46. The frame 46 may have a series of grooves 152 to accommodate drivers of different lengths. The collar 128 has a recess 154 for receiving the second end 132 of the driver 124. The collar 128 may have an annular groove 156 formed in the recess 154 for receiving the retaining member 144 of the cap 139 in a way that releasably captures the driver 124 to hold the driver 124 in the retracted position relative to the drive shaft 122. The collar 139 has a face 158 extending about the recess 154 which is engageable with a first stop member 159a extending from the frame 46 to permit the driver 124 to be released from the collar 128 and thus permit the driver 124 to extend relative to the drive shaft 122 due to the force applied by the biasing member 126. The frame 46 may have a second stop member 159b extending from the frame 46 to support the proximal end 80 of the drive assembly 52.

The apparatus 40 has a drive mechanism 160 for selectively powering the drive assembly 52 in a clockwise direction and a counterclockwise direction. In the example shown, the drive mechanism 160 is selectively coupled and decoupled to the drive assembly 52 by movement of the drive assembly 52.

The drive mechanism 160 is provided with a plurality of triggers 162-1 and 162-2, switches 164-1 and 164-2, a controller 166, a relay 168, a motor 170 and a power linkage 172, all of which are connected to the frame 46. The triggers 162-1 and 162-2 are located adjacent to the handle 47 and extend outwardly from the frame 46 so as to be engageable by a user. The triggers 162-1 and 162-2 are connected to the switches 164-1 and 164-2 and permit a user to selectively actuate the switches 164-1 and 164-2 to control the speed and direction of rotation of the drive assembly 52.

Actuation of the switch 164-1 causes the motor 170 to rotate the drive assembly 52 in clockwise direction, and actuation of the switch 164-2 causes the motor 170 to rotate the drive assembly 52 in a counterclockwise direction. The switches 164-1 and 164-2 can be implemented as rheostats or potentiometers, having one or two leads connected to the controller 166. The switches 164-1 and 164-2 provide electrical signals to the controller 166, typically based upon a variable amount of resistance, that are indicative of the force applied to the triggers 162-1 and 162-2 by the user or preset with a torque limit setting.

The controller 166 receives and interprets the signals and generates control signals that the controller 166 delivers to the relay 168 to indirectly control the motor 170. The controller 166 may have analog to digital converters converting the electrical signals to digital values, and may also use a look-up table to create the control signals. The relay 168 has an input circuit connected to the controller 166, and an output circuit connected to the motor 170 and a power source 174, which can be a rechargeable or non-rechargeable battery power source, for example. The relay 168 translates the control signals from the controller 166 into a voltage having a desired magnitude and polarity to be supplied to the motor 170 by the power source 174. The relay 168 can be implemented in a variety of manners including a contactor, a solid state relay, or an electrically operated switch.

Upon actuation, the motor 170 causes the power linkage 172 to rotate in either a clockwise direction or a counterclockwise direction depending upon the state of the triggers 162-1 and 162-2. The power linkage 172 includes a power coupler 175, such as a gear, that is positioned and configured to couple power to the power coupler 120 of the drive assembly 52 when the drive assembly 52 is in the driving position.

As discussed above, the apparatus 40 is designed to engage and retract multiple instruments 48 in a sequential process (i.e., awl 48-1, drill bit 48-2, and tap 48-3) to form the threaded hole in the bone 42. To assist in the sequential engagement and retraction of multiple instruments 48, the apparatus 40 is provided with a stop mechanism 180 that is configured to prevent the instruments 48 from inadvertently exiting the barrel 68 and decoupling from the distal end 82 of the drive assembly 52.

In the embodiment shown in FIGS. 3-7, the stop mechanism is implemented as a pair of springs or pins 182-1 and 182-2 located adjacent to the distal end 74 of the barrel 68. The pins 182-1 and 182-2 are supported by the barrel 68 and are movable in a direction substantially normal to the longitudinal passage 76 in a way that the pins 182-1 and 182-2 can be positioned within the longitudinal passage 76 and retracted from the longitudinal passage 76. The stop mechanism may also include a button 180 (FIG. 2) to permit a user to move the pins into the longitudinal passage 76, and a spring (not shown) to bias the pins 182-1 and 182-2 out of the longitudinal passage 76.

Figure 8:
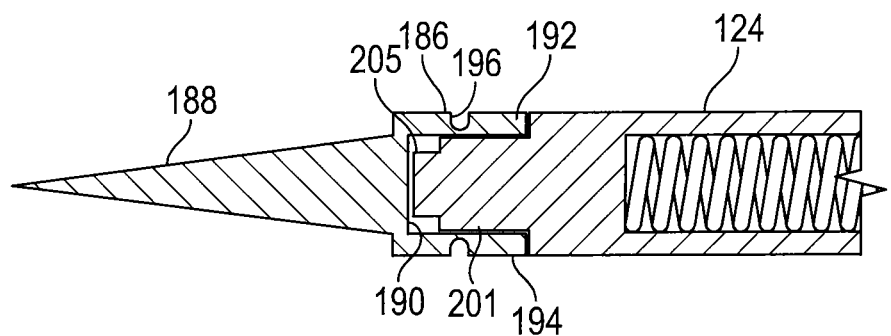
FIG. 8 is a cross-sectional view of the bit and first tip portion of the drive assembly positioned within the head of the instrument.

As shown in FIG. 8, the instruments 48 have a head portion 186 and a tool portion 188. The head portion 186 is provided with a front wall 190 that is connected to and supports the tool portion 188, and a sidewall 192 extending from the front wall 190. The sidewall 192 may be in the form of a cylinder having an outer surface 194. In the embodiment shown, the outer surface 194 is shaped to include an annular groove 196 extending about the circumference of the outer surface 194. When the driver 124 is positioned in the driving position and the annular groove 196 is positioned adjacent to the pins 182-1 and 182-2, the pins 182-1 and 182-2 can be moved into the longitudinal passage 76 to ride in the annular groove 196. When the pins 182-1 and 182-2 are in this position, the instrument 48 cannot be moved longitudinally within the barrel 68. To retract the driver 124 from the driving position, the pins 182-1 and 182-2 are moved out of the longitudinal passage 76 thereby disengaging the pins 182-1 and 182-2 from the sidewall 192, and then moving the slide 86 rearwardly. The annular groove 196 also receives the retaining member 67 to releasably secure the instrument 48 in the chamber 64.

Figure 9:
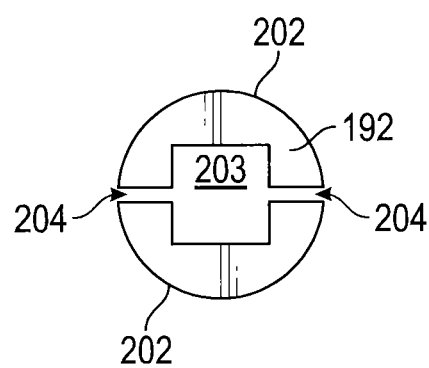
FIG. 9 is a top view of a head of an instrument configured as a return mechanism in which the head has a cavity shaped to mate with and grip the first tip portion of the drive assembly in accordance with the presently disclosed inventive concepts.

To permit the drive assembly 52 to rotate and retract the instruments 48, the head portion 186 includes a return mechanism 200 as shown in FIG. 9. The return mechanism 200 removably couples a first tip portion 201 of the driver 124 to the head portion 186 to permit the driver 124 to return the instrument 48 into the chamber 64 in the use position during movement of the drive assembly 52 from the driving position to the engaging position. The first tip portion 201 is adjacent to, but spaced a distance from, the distal end 82 of the driver 124.

In the embodiment shown in FIGS. 8 and 9, the return mechanism 200 is implemented as a plurality of adjacently disposed flexible fingers 202 that form the sidewall 192. The head portion 186 defines an opening 203 that is surrounded by the flexible fingers 202 that form the sidewall 192. The opening 203 matingly receives the first tip portion 201 so that the flexible fingers 202 can grip the first tip portion 201. Further, the opening 203 is provided with a non-circular shape (e.g., square, rectangular) so that rotation of the first tip portion 201 causes the first tip portion 201 to engage the flexible fingers 202 and rotate the instrument 48. The fingers 202 are interleaved with slots 204 that permit the fingers 202 to move relative to each other thereby gripping the first tip portion 201 of the driver 124 when the driver 124 engages the head portion 186. Although two fingers 202 and two slots 204 are shown in FIG. 9, it should be understood that the return mechanism 200 can be provided with more than two fingers 202 and slots 204. The driver 124 also has a second tip portion 205 connected to and extending from the first tip portion 201. The opening 203 of the instrument is provided with a depth into the head portion 186 that exceeds a length of the second tip portion 205 so that the flexible fingers 202 engage the first tip portion 201 rather than the second tip portion 205. Further, in the example shown, the opening 203 is shaped so as to not matingly engage the second tip portion 205. This can be done by providing the opening 203 with a consistent width throughout the depth of the opening 203, as shown in FIG. 8.

Figure 10:
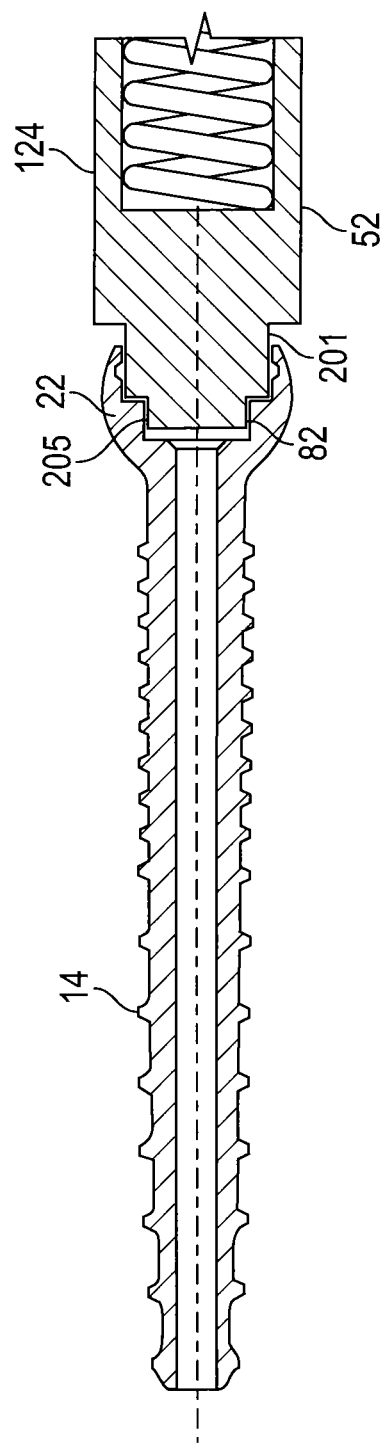
FIG. 10 is a cross-sectional view of the drive assembly having a bit and a first tip portion and with the bit of the drive assembly engaging an implant.

FIG. 10 is a cross-sectional view of a distal end of the driver 124 having the second tip portion 205 connected to and extending from the first tip portion 201. The second tip portion 205 of the driver 124 engages the implant 50, which in this example is the first implant 14. The second tip portion 205 extends from the first tip portion 201 and is engageable with the implant 50 in a way that permits rotation of the first implant 14 but does not encourage retraction of the first implant 14 from the distal end 74 of the barrel 68 upon moving the driver 124 from the driving position to the retracted position. In this example, this is accomplished by designing the enlarged head portion 22, to have a mating fit (e.g., a square drive, phillips drive, or star drive) with the second tip portion 205, but for such fit to be relatively loose so that the enlarged head portion 22 is loosely fit (e.g., not press-fit) to the second tip portion 205, and also unable to be gripped by the first tip portion 201.

In one embodiment, the first tip portion 201 and the second tip portion 205 are different in size and shape. By way of example, the first tip portion 201 may be shaped as a square and the second tip portion 205 may be shaped as a star with a diameter less than the diameter of the first tip portion 201. However, it will be appreciated that the shape of the first tip portion 201 and the second tip portion 205 may be any shape that is matingly engageable with a corresponding shape of the opening 203 of the instrument 48 and the implant 50.

Returning to FIG. 2, to prevent inadvertent movement of the apparatus 40 relative to the bone 42, the frame 46 is also provided with a plurality of anchoring spikes 210-1, 210-2 and 210-3 configured to engage and pierce the bone 42. The anchoring spikes 210-1, 210-2 and 210-3 are connected to and extend from the distal end 74 of the barrel 68.

One skilled in the art will recognize that the apparatus 40 can have many optional features and/or be designed in other ways. For example, the apparatus 40 can be provided with an angle meter 220 located on a rear end 222 of the frame 46 so that the angle meter 220 is visible to a user. The apparatus 40 can also be provided with a navigational or telemetry system 226 so as to permit the three-dimensional position of the apparatus 40 to be recorded in real-time during use of the apparatus 40. The apparatus 40 can also be provided with a light and laser pointer 230 and a camera 231 positioned on the barrel 68 to assist the user in forming the threaded hole. Although the cartridge 44 has been shown and described as having a cylindrical shape, it should be understood that the cartridge 44 can be provided with other shapes. For example, the cartridge 44 can be designed with a substantially rectangular shape designed to move in a linear fashion (e.g., either side to side or up and down) within the frame 46. In this example, the chambers 64 would be offset linearly from one another. Further, although the apparatus 40 is described as forming a threaded hole within the bone 42, it should be understood that the hole does not have to be a threaded hole. For example, the awl 48-1 and the drill bit 48-2 can be used to form an unthreaded hole. In this embodiment, the implant 50 may have self-tapping threads which forms threads in the bone 42 as the implant 50 is inserted into the unthreaded hole formed in the bone 42 by the apparatus 40.

Operation

Prior to forming a threaded hole, the cartridge 44 is prepared by positioning at least one of the instruments 48-1, 48-2 and 48-3 and the implants 50 into the respective chambers 64 of the cartridge 44. In the embodiment shown in FIG. 2, the chambers 64 intersect an outer surface of the cartridge 44 so that the instruments 48-1, 48-2 and 48-3 and implants 50 are visible to the user so that the user will know and understand which of the instruments 48-1, 48-2 and 48-3 and implants 50 is in the use position. The cartridge 44 having the instruments 48-1, 48-2 and 48-3 and the implants 50 is positioned within the container 77-1, and the container 77-1 is sealed. This can be accomplished by applying the removable tab 77-2 to the container 77-1.

The cartridge 44, the implant(s) 50 and the instrument(s) 48 can be sterilized prior to or after the container 77-1 is sealed. For example, the cartridge 44, the implant(s) 50 and the instrument(s) 48 can be sterilized by treating with steam or a suitable biocide prior to insertion into the container 77-1. Or, the cartridge 44, the implant(s) 50, the instrument(s) 48 and the container 77-1 can be sterilized by being subjected to an environment of at least 200 degrees Fahrenheit for a period of time suitable to kill or deactive any microorganisms within the container 77-1.

As shown in FIGS. 3-7, to form the threaded hole, the apparatus 40 is designed to engage and retract multiple instruments 48 in a sequential process (i.e., awl 48-1, drill bit 48-2 and tap 48-3) and then to place the implant 50 into the threaded hole. As shown in FIG. 3, this can be accomplished by moving the slide 86 to place the drive assembly 52 in the retracted position wherein the driver 124 is captured by the collar 128. The cartridge 44 is then rotated to initially place the chamber 64 housing the awl 48-1 in the use position.

As illustrated in FIG. 4, initial forward movement the slide 86 causes the protrusion 104 of the slide 86 to disengage from the retainer member 137 and travel toward and contact the annular shoulder 136. Due to the contact of the protrusion 104 with the annular shoulder 136, continued forward movement of the slide 86 causes the driver 124 to release from the collar 128 to permit the driver 124 to move into engagement with the awl 48-1 (FIG. 5). Release of the driver 124 from the collar 128 also allows the biasing member 126 to extend the driver 124 relative to the drive shaft 122, as shown in FIG. 6. Movement of the slide 86 is continued until the slide 86 reaches a forward position, as illustrated in FIG. 5. Extension of the driver 124 by the biasing member 126 moves the awl 48-1 into the driving position where it is captured by the pins 182-1 and 182-2 of the stop mechanism (FIG. 6). The awl 48-1 is then used to form a pilot hole in the bone 42 by manipulating the handle 47.

With the pilot hole formed, the awl 48-1 may be returned to the retracted position. First, the pins 182-1 and 182-2 of the stop mechanism are disengaged from the awl 48-1. Next, the slide 86 is moved in a rearward direction causing the protrusion 104 to engage the retaining member 137 on the driver 124, as illustrated in FIG. 6. Continued rearward movement of the slide 86 causes the awl 48-1 to be pulled back into the chamber 64 and re-engaged by the retaining members 67 in a way that continued rearward movement of the drive assembly 52 causes the driver 124 to release from the awl 48-1 due to the support provided to the instrument 48 by the retaining members 67. Further rearward movement of the slide 86 causes the proximal end 80 of the drive assembly 52 to contact the second stop member 159*b*. Still further rearward movement of the slide 86 causes the driver 124 to re-engage with the collar 124 and secure the driver 124 in the retracted position with the biasing member 126 in a compressed state (FIG. 3).

This process may then be repeated for the drill bit 48-2 and the tap 48-3 rotating the cartridge 44 to place the desired instrument 48 in alignment with the drive assembly 52. Unlike with use of the awl, after the drill bit 48-2 and the tap 48-3 are captured with the pins 182-1 and 182-2 of the stop mechanism, the user engages the appropriate one of the triggers 162-1 or 162-2 to actuate the drive assembly 52 and thus cause the drill bit 48-2 and the tap 48-3 to rotate and cut the hole within the bone 42.

At this point, the apparatus 40 has formed a threaded without a user having to touch or directly handle any of the instruments 48 including but not limited to the awl 48-1, the drill bit 48-2, or the tap 48-3.

Once the threaded hole has been formed, the slide 86 is then moved rearwardly to retract the tap 48-3 and place the drive assembly 52 in the retracted position such that the drive assembly 52 is outside of the chamber 64 while maintaining the anchoring spikes 210-1, 210-2 and 210-3 against the bone 42. The cartridge 44 is moved to place the chamber 64 housing one of the implants 50 in the use position and the slide 86 is moved forward to engage the implant 50 and carry the implant 50 to the threaded hole. In use of the implant, the distal end of the implant will be received in the top of the threaded hole with the driver 124 biased toward the threaded hole. The user engages the appropriate one of the triggers 162-1 or 162-2 to actuate the drive assembly 52 and cause the implant 50 to rotate and engage with the threaded hole. Because the driver 124 is biased by the biasing member 126, the driver 124 is moved in the forward direction to remain engaged with the implant 50 and drive the implant 50 into the threaded opening. When the implant 50 is inserted as desired, the slider 86 is moved in the rearward direction causing the driver 124 to disengage from the implant 50, which is secured in the bone 42. The process is repeated for each implant 50 to be implanted.

While the apparatus 40 has been described above for use with a cartridge housing multiple instruments and multiple implants, it should be appreciated that the cartridge may include only instruments of various types (i.e., no implants). Alternatively, the cartridge may contain only implants of the same or varying lengths and the same or varying geometries (i.e., screws, set screws, self-tapping screws, pedicle screws, locking caps) which the drive assembly 52 advances into bone and/or into another implant.

The materials used to construct the apparatus 40 are those which have sufficient strength and biocompatibility, and are well known in the art for such devices. By way of example only, suitable materials include titanium, titanium alloys including Nitinol, and stainless steel. The cartridge 44 and instruments 48 may be single use devices and may be disposed of after use.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims.

What is claimed is:

1. An apparatus for inserting implants in a bone, comprising:
   a frame having a cartridge receiving chamber and a barrel, the barrel having a sidewall, a proximal end, a distal end, and a longitudinal passage extending through the barrel from the proximal end to the distal end;
   a single cartridge defining a plurality of chambers extending through the cartridge in a parallel relationship to one another, the cartridge positioned in the cartridge receiving chamber of the frame so as to be movable relative to the barrel in a way that each of the chambers is selectively alignable with the longitudinal passage of the barrel;
   at least one instrument positioned in a selected one of the chambers of the cartridge, the instrument configured for making a hole in the bone;
   a plurality of implants positioned in selected ones of the chambers of the cartridge, each of the implants configured to be fixed within the hole formed in the bone by the instrument;
   the barrel being configured to receive and position a selected instrument or implant for use at a distal end of the barrel; and
   a drive assembly having a proximal end, a distal end and a longitudinal axis, the longitudinal axis aligned with the longitudinal passage extending through the barrel, the distal end of the drive assembly being engageable with the instrument and the implants, the drive assembly being slidably and rotatably disposed in the frame in a way that the drive assembly is moveable between a retracted position wherein the drive assembly is positioned to permit the cartridge to be moved so as to align a selected one of the instrument or the implant with the longitudinal passage of the barrel, an engaging position wherein the distal end of the drive assembly is positioned to engage the selected one of the instrument and the implants positioned within the chamber aligned with the longitudinal passage of the barrel, and an extended position wherein the drive assembly is extended through the chamber aligned with the longitudinal passage of the barrel to transport the selected one of the instrument or the implant from the chamber to the distal end of the barrel where the drive assembly is rotatable to apply a rotational force to the selected one of the instrument or the implant.

2. The apparatus of claim 1, wherein the drive assembly includes a driver having a proximal end and a distal end, and wherein the distal end of the driver is engageable with the instrument in a way that the instrument is moveable from the distal end of the barrel to the chamber aligned with the longitudinal passage of the barrel upon moving the driver from the extended position to the retracted position.

3. The apparatus of claim 1, wherein the distal end of the driver has a first tip portion matingly engageable with the instrument and a second tip portion matingly engageable with the implant, wherein the second tip portion extends from the first tip portion, and wherein the first tip portion and the second tip portion are different in size.

4. The apparatus of claim 3, wherein the first tip portion and the second tip portion are different in shape.

5. The apparatus of claim 1, wherein the at least one instrument is defined further as a plurality of instruments, each of the instruments being positioned in a selected one of the chambers of the cartridge, and wherein one of the instruments is an awl, one of the instruments is a drill bit, and one of the instruments is a tap.

6. The apparatus of claim 1, wherein the implants are pedicle screws.

7. The apparatus of claim 1, wherein the drive assembly includes a driver and a drive shaft, and wherein the driver is connected to the drive shaft in a telescoping relationship such that the driver is positionable between a retracted position and an extended position relative to the drive shaft.

8. An apparatus for inserting implants in a bone, comprising:
a frame having a cartridge receiving chamber and a barrel, the barrel having a sidewall, a proximal end, a distal end, and a longitudinal passage extending through the barrel from the proximal end to the distal end;
a single cartridge defining a plurality of chambers extending through the cartridge in a substantially parallel relationship to one another, the cartridge positioned in the cartridge receiving chamber of the frame so as to be movable relative to the barrel in a way that each of the chambers is selectively alignable with the longitudinal passage of the barrel;
a drill bit positioned in one of the chambers of the cartridge, the drill bit having an instrument head and an instrument shaft configured for making a hole in the bone;
a plurality of screws positioned in selected ones of the chambers of the cartridge, each of the screws having an implant head and an implant shaft configured to be implanted in the bone; and
a drive assembly having a proximal end and a distal end, the distal end of the drive assembly being engageable with the drill bit and the screws, the drive assembly slidably and rotatably disposed in the frame in a way that the drive assembly is moveable between a retracted position wherein the drive assembly is positioned to permit the cartridge to be moved so as to align a selected one of the drill bit and the screws with the longitudinal passage of the barrel, an engaging position wherein the distal end of the drive assembly is positioned to engage the selected one of the drill bit and the screw positioned within the chamber aligned with the longitudinal passage of the barrel, and an extended position wherein the drive assembly is extended through the chamber aligned with the longitudinal passage of the barrel to transport the selected one of the drill bit and the screw from the chamber to the distal end of the barrel where the drive assembly is rotatable relative to the barrel to apply a rotational force to the selected one of the drill bit and the screw.

9. The apparatus of claim 8, wherein the drive assembly includes a driver having a proximal end and a distal end and wherein the distal end of the driver is engageable with the drill bit in a way that the drill bit is moveable from the distal end of the barrel to the chamber aligned with the longitudinal passage of the barrel upon moving the driver from the extended position to the retracted position.

10. The apparatus of claim 8, wherein the drive assembly includes a driver having a proximal end and a distal end and wherein the distal end of the driver has a first tip portion matingly engageable with the instrument and a second tip portion matingly engageable with the implant, wherein the second tip portion extends from the first tip portion, and wherein the first tip portion and the second tip portion are different in size.

11. The apparatus of claim 10, wherein the first tip portion and the second tip portion are different in shape.

12. The apparatus of claim 8, further comprising an awl being positioned in a selected one of the chambers of the cartridge.

13. The apparatus of claim 8, wherein the screws are pedicle screws.

14. The apparatus of claim 8, further comprising anchoring spikes connected to and extending from the distal end of the barrel.

15. The apparatus of claim 8, wherein the drive assembly includes a driver and a drive shaft, and wherein the driver is connected to the drive shaft in a telescoping relationship such that the driver is positionable between a retracted position and an extended position relative to the drive shaft.

16. An apparatus for inserting implants in a bone, comprising:
a frame having a cartridge receiving chamber and a barrel, the barrel having a sidewall, a proximal end, a distal end, and a longitudinal passage extending through the barrel from the proximal end to the distal end;
a cartridge defining a plurality of chambers extending through the cartridge in a substantially parallel relationship to one another, the cartridge positioned in the cartridge receiving chamber of the frame so as to be movable relative to the barrel in a way that each of the chambers is selectively alignable with the longitudinal passage of the barrel;
a plurality of screws positioned in selected ones of the chambers of the cartridge, each of the screws having an implant head and an implant shaft configured to be implanted in the bone; and
a drive assembly having a proximal end and a distal end, the distal end of the drive assembly being engageable with the screws, the drive assembly slidably and rotatably disposed in the frame in a way that the drive assembly is moveable between a retracted position wherein the drive assembly is positioned to permit the cartridge to be moved so as to align a selected one the screws with the longitudinal passage of the barrel, an engaging position wherein the distal end of the drive assembly is positioned to engage the selected one of the screw positioned within the chamber aligned with the longitudinal passage of the barrel, and an extended position wherein the drive assembly is extended through the chamber aligned with the longitudinal passage of the barrel to transport the selected one of the screw from the chamber to the distal end of the barrel where the drive assembly is rotatable relative to the barrel to apply a rotational force to the selected one of the screw,
wherein the drive assembly includes a driver and a drive shaft, and
wherein the driver is connected to the drive shaft in a telescoping relationship such that the driver is positionable between a retracted position and an extended position relative to the drive shaft.

* * * * *